United States Patent
Marini et al.

(10) Patent No.: US 10,034,825 B2
(45) Date of Patent: Jul. 31, 2018

(54) LUMINATE EYE GEL

(71) Applicant: Jan Marini Skin Research, San Jose, CA (US)

(72) Inventors: Jan L. Marini, San Jose, CA (US); Subhash J. Saxena, Ringoes, NJ (US)

(73) Assignee: Jan Marini Skin Research, San Jose, CA (US)

(*) Notice: Subject to any disclaimer, the term of this patent is extended or adjusted under 35 U.S.C. 154(b) by 194 days.

(21) Appl. No.: 14/789,566

(22) Filed: Jul. 1, 2015

(65) Prior Publication Data

US 2017/0000716 A1 Jan. 5, 2017

(51) Int. Cl.

| | |
|---|---|
| A61K 8/64 | (2006.01) |
| A61K 8/49 | (2006.01) |
| A61K 8/36 | (2006.01) |
| A61K 8/34 | (2006.01) |
| A61K 8/42 | (2006.01) |
| A61K 8/04 | (2006.01) |
| A61Q 19/08 | (2006.01) |
| C07K 1/107 | (2006.01) |

(52) U.S. Cl.
CPC .............. *A61K 8/64* (2013.01); *A61K 8/042* (2013.01); *A61K 8/342* (2013.01); *A61K 8/361* (2013.01); *A61K 8/42* (2013.01); *A61K 8/498* (2013.01); *A61K 8/4913* (2013.01); *A61Q 19/08* (2013.01); *A61K 2800/5922* (2013.01); *C07K 1/1077* (2013.01)

(58) Field of Classification Search
None
See application file for complete search history.

(56) References Cited

U.S. PATENT DOCUMENTS

| | | | |
|---|---|---|---|
| 5,914,116 A * | 6/1999 | Suares | A61K 8/02 424/401 |
| 6,821,524 B2 | 11/2004 | Marini | |
| 8,318,678 B2 | 11/2012 | Marini | |
| 2007/0196318 A1 | 8/2007 | Marini | |
| 2008/0152680 A1* | 6/2008 | Brown | A61K 8/042 424/401 |
| 2008/0213198 A1* | 9/2008 | Lintner | A61K 8/361 514/1.1 |
| 2009/0263513 A1 | 10/2009 | Marini | |
| 2010/0247693 A1 | 9/2010 | Marini | |
| 2013/0171119 A1* | 7/2013 | Marini | A61K 8/355 424/94.1 |
| 2013/0189211 A1 | 7/2013 | Marini | |
| 2013/0195925 A1* | 8/2013 | Arshed | A61K 8/97 424/400 |
| 2014/0228291 A1 | 8/2014 | Subhash et al. | |

FOREIGN PATENT DOCUMENTS

| | | |
|---|---|---|
| EP | 1203579 A1 | 5/2002 |
| EP | 1369107 A1 | 12/2003 |
| EP | 1825845 A1 | 8/2007 |
| WO | 2009/148551 A1 | 12/2009 |

* cited by examiner

*Primary Examiner* — Marcela M Cordero Garcia
*Assistant Examiner* — Jia-Hai Lee
(74) *Attorney, Agent, or Firm* — Pamela J. Sherwood; Bozicevic, Field & Francis LLP

(57) ABSTRACT

The present invention features novel cosmetic skin care compositions for improving the appearance of skin, particularly the periocular region.

16 Claims, 1 Drawing Sheet
(1 of 1 Drawing Sheet(s) Filed in Color)

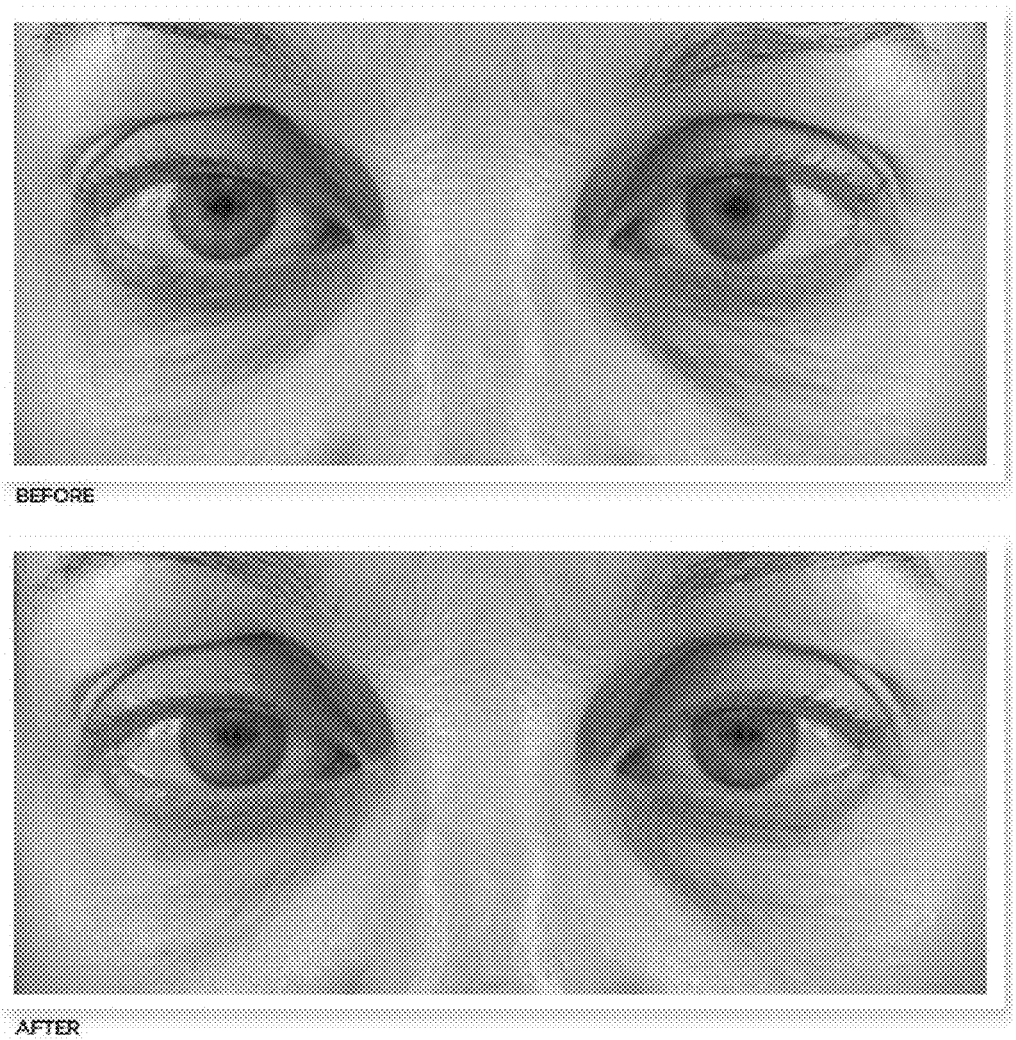

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

```
<220> FEATURE:
<221> NAME/KEY: MOD_RES
<222> LOCATION: (1)...(1)
<223> OTHER INFORMATION: conjugation to palmitate

<400> SEQUENCE: 1

Gly Gln Pro Arg
 1
```

LUMINATE EYE GEL

BACKGROUND OF THE INVENTION

The skin provides the first barrier to the external environment, and as such it is continually subjected to stresses such as extreme heat or cold, attack by microorganisms, exposure to UV radiation, abrasion, chemical irritants and the like. As a result, the skin can show signs of response to damage over time, for example fine lines and wrinkles, sunburn, roughening, discoloration, and even malignancies. While these effects are often considered to be normal aging, in fact, they are not normal results of aging but are responses to damage.

A myriad of changes are associated with aging, ranging from hormonal changes to the effects of cumulative sun damage to the continued effects other environmental and social stresses. The signs of progressive aging begin to manifest in the mid 20s, and continue to increase with time. Some of the changes associated with aging included decreased epidermal (top layer of skin) cell turnover; impaired barrier function in the skin leading to moisture loss and risk of irritation; thinning of the dermis; thinning and reduction in elastin fibers (provides skin elasticity); changes and reduction in collagen fibers (structure of the skin); decreased vascular supply to the surface of the skin; cumulative sun damage; significant decline in the skin's immune function inhibiting cellular repair; inflammation and free radical activity causing cellular damage and abnormalities; discoloration, uneven pigment distribution and gradual loss of skin translucency.

The skin around the eyes also known as the periocular area, is ten times thinner than the skin on the face. Facial movements and expressions such as smiles, squinting, and stress can affect the eye area, creating fine lines or crow's feet. Under eye puffiness can also be evident; and rubbing and tugging of the delicate skin in this area can contribute to sagging of the this area. Because the tissue around the eyes has very few oil glands, it lacks the natural moisture present on other parts of the body. Because the skin around the eyes is thinner, it tends to be the first place to show signs of aging, however it is also particularly sensitive, and needs extra care when treated with products.

The periocular area skin is easily susceptible to wrinkles, fine lines, dark circles, and crow's feet with time. The present invention provides a cosmetic formulation to address this issue.

SUMMARY OF THE INVENTION

The present invention provides cosmetic formulations for improving the appearance of the skin, including the periocular area. Specifically designed for the delicate eye area, the compositions of the invention reduce the appearance of under eye circles and discoloration while firming crepey skin and improving the appearance of fine lines and wrinkles. The composition is topically administered as a gel or cream for a period of time sufficient to accomplish the desired effect. In some embodiments the composition is administered once daily, or twice daily, and for at least about one week, at least about two weeks, at least about one month, or longer as desired.

Specifically, the skin care compositions presented herein contain a combination of agents that brighten skin and reduce discoloration, reduce wrinkles, reduce puffiness and improve hydration. These agents are combined in a cosmetic formulation, particularly a gel formulation, e.g. one or a mixture of cyclic siloxanes, which may be a defined mixture of specific length siloxanes, e.g. cyclotetrasiloxane, cyclopentasiloxane, cyclohexasiloxane, cycloheptasiloxane, etc., which may further comprise skin soothing/conditioning agents. Accordingly, the combinations of the active ingredients of the invention are formulated as skin care cosmetic compositions that can be applied directly to the skin so as to improve the appearance of skin texture and color. The compositions may additionally provide cosmetic benefit for aging skin, spider veins, and sun damage.

According to the first aspect of the invention, there is provided a cosmetic composition comprising a specific and efficacious blend of moisturizing agents, including skin brightening agents dimethylmethoxy chromanyl palmitate, palmitoyl tetrapeptide-7, and palmitoyl tripeptide-1. The composition may further comprise an effective dose of chrysin as a skin brightening agent. The composition may further comprise an effective dose of N-hydroxy-succinimide as a skin brightening agent. In some embodiments the composition comprises agents to reduce wrinkles, e.g. retinol; and hydrating agents, e.g. ceramide-2 and tocopherol.

In the second aspect of the invention, a method is provided for improving the appearance of the skin, in particular for firming and improving the appearance of the skin of the periocular area, the method comprising applying topically a cosmetic composition comprising: skin brightening agents dimethylmethoxy chromanyl palmitate, palmitoyl tetrapeptide-7, and palmitoyl tripeptide-1. The composition may further comprise an effective dose of chrysin as a skin brightening agent. The composition may further comprise an effective dose of N-hydroxy-succinimide as a skin brightening agent. In some embodiments the composition comprises agents to reduce wrinkles, e.g. retinol; and hydrating agents, e.g. ceramide-2 and tocopherol.

BRIEF DESCRIPTION OF THE DRAWING

The patent or application file contains one drawing executed in color. Copies of this patent or patent application publication with color drawing will be provided by the Office upon request and payment of the necessary fee.

FIG. 1 provides a before and after comparison after use of the agents of the invention.

DETAILED DESCRIPTION OF THE EMBODIMENTS

Topical compositions are provided for improving the appearance of the skin, including the delicate skin of the periocular area. The cosmetic formulations improve the appearance of signs of aging, including softening the appearance of deep wrinkles and creases; reducing the appearance of fine lines; and improving texture of the skin. The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders. The cosmetically acceptable vehicle will usually form 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art. In some embodiments a gel formulation is preferred.

When the compositions of the invention are formulated as a gel, the gel may comprise a blend of cyclic siloxanes (for example n=4-7). Cyclomethicone is a mixture, while cyclotetrasiloxane (n=4), cyclopentasiloxane (n=5), cyclohexasiloxane (n=6), and cycloheptasiloxane (n=7) have a defined chain length. For a review, see Johnson et al., Cosmetic Ingredient Review. Of particular interest is cyclopentasiloxane (decamethylcyclopentasiloxane), cyclohexasiloxane, and cyclotetrasiloxane. The compositions of the invention may comprise from about 75% to about 85% of the total volume as one or a combination of cyclic dimethyl polysiloxanes.

The compositions of the invention may further comprise cosmetically useful agents and excipients, e.g. glyceryl stearate, dimethicone, butylene glycol, glycerin, gransil EP-9, plurol diisosteraque, etc. each at a concentration of from about 0.5% to about 10% by weight, usually from about 0.5% to about 5%, and may be present at a concentration of from about 0.5%, 1%, 2%, 3%, 4%, 5%, etc.

Components of the Cosmetic Compositions

The compositions of the invention comprise a specific blend of therapeutic agents. Dimethylmethoxy chromanyl palmitate (CAS RM-C255) may be present in the composition at a final concentration of from about 0.025% to about 1% by weight, usually about 0.05 to 0.5% and may be present at about 0.1% by weight. Dimethylmethoxy chromanyl palmitate (INCI name) is a novel skin brightener that has been tested for efficacy and safety with satisfactory results. The agent does not have any of the side effects that are normally associated with depigmenting agents, presents good efficacy in vitro and in vivo and is unique in that, unlike all other skin brighteners, it has a photoprotective effect.

Peptides, including but not limited to, di-, tri-, tetra-, and pentapeptides, as well as oligo-peptides of from about 3 to about 10 amino acids in length and derivatives thereof, comprising at least one lipid moiety, which moiety may be myristoyl, palmitoyl, etc., may be included in compositions of the present invention in amounts that are safe and effective. The formulation comprises an effective dose of one or more such acylated peptides, which peptides are active in remodeling of the skin.

Peptides of particular interest stimulate macromolecules of the dermis, e.g. fibronectin, collagen, and the like. The stimulatory activity of the peptides provides for an improved activity in enhancing the appearance of the skin. In some embodiments, the acylated peptide is a palmitoylated peptide (e.g., palmitoyl tetrapeptide-7, palmitoyl tripeptide-1, etc.) The commercially available blend Haloxyl from Sederma Corporation may be used, for example comprising an association of 2 palmitoylated matrikines: Palmitoyl-Gly-His-Lys and (SEQ ID NO:1) Palmitoyl-Gly-Glu-Pro-Arg, see WO 2005/048968, herein specifically incorporated by reference.

The peptide agents of the present invention are formulated at an effective concentration within the subject cosmetic compositions, meaning at a concentration that provides the intended benefit when applied topically. An effective concentration of peptide or peptide-like compounds is preferably in a range of at least about 0.0001% to about 0.01, usually about 0.0001% to about 0.0005%; and each peptide may be present at a concentration of about 0.0001 to 0.0002%.

Chrysin (5,7-Dihydroxy-2-phenyl-4H-chromen-4-one, CAS number 480-40-0) is a naturally occurring flavone, a type of flavonoid. It is found in the passion flowers *Passiflora caerulea* and *Passiflora incarnata*, and in *Oroxylum indicum*. It may be present in the composition at a concentration of from about 0.0001 to about 0.01%, usually from about 0.0001% to about 0.001%, and may be present at a concentration of about 0.0002%. Chrysin is commercially available from a number of sources, or can be provided as a component of Haloxyl from Sederma Corporation.

N-hydroxysuccinimide (2,5-Pyrrolidinedione, CAS number 6066-82-6) is a skin conditioning agent that also reduces discoloration of the skin. It may be present in the composition at a concentration of from about 0.0005% to about 0.05%, usually from about 0.001% to about 0.01%, and may be present at a concentration of about 0.004%.

Tocopherol acetate is the ester of acetic acid and tocopherol (vitamin E). Tocopheryl acetate is not oxidized and can penetrate through the skin to the living cells, where about 5% is converted to free tocopherol and provides beneficial antioxidant effects. It may be present in the composition at a concentration of from about 0.05 to about 1% by weight, usually from about 0.25% to about 0.75%, and may be present at a concentration of about 0.5%. Tocopheryl acetate is known in the art and commercially available under CAS # 7695-91-2 from various suppliers.

Retinol, CAS number 68-26-8, (2E,4E,6E,8E)-3,7-dimethyl-9-(2,6,6-trimethylcyclohex-1-enyl) nona-2,4,6,8-tetraen-1-ol, may be present at a concentration of from 0.05% to about 0.5%, usually from about 0.01% to about 0.075%, and may be about 0.03% by weight.

Linoleic acid (LA), CAS number 60-33-3, is a polyunsaturated omega-6 fatty acid. It is a colorless liquid at room temperature. It may be present in the composition at a concentration of from about 0.05% to about 5%, usually from about 0.1% to about 1%, and may be present at about 0.37%.

Linolenic acid, CAS Number 463-40-1, can refer to either of two octadecatrienoic acids (i.e. with an 18-carbon chain and three double bonds, which are found in the cis configuration), or a mixture of the two. Linolenate (in the form of esters of linolenic acid) is often found in vegetable oils. It may be present in the composition at a concentration of from about 0.025% to about 1%, usually from about 0.05% to about 0.25%, and may be present at about 0.1%.

Ceramide-2 (N-acetyl sphingosine, CAS 3102-57-6) is a cell-permeable analog of naturally occurring ceramides. It is commercially available, e.g. from Cayman Chemical. It may be present in the composition at a concentration of from about 0.0005% to about 0.05%, usually from about 0.001% to about 0.01%, and may be present at a concentration of about 0.002%.

The compositions of the invention may optionally comprise other skin benefit materials. These include estradiol; progesterone; pregnanalone; coenzyme Q10; methylsolanomethane (MSM); copper peptide (copper extract); plankton extract (phytosome); kojic acid; broparoestrol; estrone; adrostenedione; androstanediols; hydroquinone; isoflavones;, etc. The steroids will generally be present at a concentration of less than about 5% or about 10% of the total by weight of the composition, while the other skin benefit materials may be present at higher levels, for example as much as about 10 to about 15%.

The compositions may further comprise sunscreens to lower skin's exposure to harmful UV rays. Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. Dermascreen, titanium dioxide or zinc oxide may also be used. The exact amount of sunscreen employed in the compositions can vary depending upon the degree of protection desired from the sun's UV radiation.

The amounts of cosmetic or dermatological auxiliaries and additives and perfume to be used in each case can easily be determined by simple exploratory experiments by the person skilled in the art, depending on the nature of the product in question.

Cosmetically Acceptable Vehicle

The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders.

The cosmetically acceptable vehicle will usually form 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions;

dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifier and co emulsifier may be present in the composition at a proportion ranging from 0.3% to 30% by weight, and preferably from 0.5% to 20% by weight, relative to the total weight of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase or into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Accordingly, a composition of the invention comprises a retinoid, a stable kojic acid derivative, and a resorcinol derivative, which may be a synergistic combination, and optionally in combination with one or more of a permeation enhancer, an azelaic acid or a derivative thereof, salicylic acid or a derivative thereof, glycolic acid or a derivative thereof, licorice extract, and green tea extract, and/or a cosmetically acceptable vehicle. Furthermore, a composition of the invention may include additional agents or additives that are not in themselves active agents but play a role in promoting the usefulness or effectiveness of an active agent.

Compositions of the invention may be applied to any subject and used to treat a variety of conditions, for example aged or sun-damaged skin of the hands, for which the compositions may provide firming, and softening of the appearance of wrinkles. A typical composition of the invention is formulated as a solution, lotion, cream, gel, ointment, liniment, solvent, emulsion, dispersion, hydrodispersion, etc., which may be applied topically to the skin so as to treat, prevent, wash, condition or otherwise effect a condition of the skin.

Product Use, Form, and Packaging

In use, a quantity of the composition, for example from 1 to 100 ml, is applied to a site of interest from a suitable container or applicator and, if necessary, it is then spread over and/or rubbed into the site using the hand or fingers or a suitable device. The product may be specifically formulated for use as a treatment for a specific area, e.g. the neck, the hands, the face, the arms, etc.

The cosmetic composition of the invention can be formulated in any form suitable for application to the site of interest, including a lotion, cream, gel, or the like. The composition can be packaged in any suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

EXAMPLE 1

Example 1 illustrates a topical composition according to the present invention. The composition can be processed in conventional manner and is suitable for cosmetic use. In particular the compositions are suitable for application to a site of interest for the treatment of a variety of skin conditions.

Marini Luminate Eye Gel

| Name | CAS number | Final concentration |
| --- | --- | --- |
| N-Hydroxysuccinimide | 6066-82-6 | 0.001-0.01% |
| Chrysin | 480-40-0 | 0.0001-0.001% |
| Palmitoyl Tripeptide-1 | N/A | 0.0001-0.001% |
| Palmitoyl Tetrapeptide-7 | N/A | 0.0001-0.0005% |
| Linoleic Acid | 60-33-3 | 0.1-1% |
| Linolenic Acid | 463-40-1 | 0.05-0.25% |
| Tocopherol acetate | 7695-91-2 | 0.1-1% |
| Retinol | 68-26-8 | 0.01-0.075% |
| Ceramide-2 | PM-C144 | 0.001-0.01% |
| Dimethylmethoxy Chromanyl Palmitate | RM-C255 | 0.05-0.5% |

Additional ingredients can be included to provide a cosmetically acceptable vehicle, and may comprise water, cyclic polysiloxanes, glycerin, caprylic/capric triglyceride, glyceryl stearate, *Butyrospermum parkii* (shea) butter, cetyl alcohol, dimethicone, cyclopentasiloxane, citric acid, *Prunus amygdalus dulcis* (sweet almond) oil, cyclohexasiloxane, *Glycine soja* (soybean) oil, sodium stearoyl glutamate, squalane, aluminum starch octenylsuccinate, pentylene glycol, sodium oleate, hydrogenated lecithin, ethyl alcohol, coco-glucoside, caprylyl glycol, sodium citrate, ethylhexylglycerin, hexylene glycol, acrylates/c10-30 alkyl acrylate crosspolymer, xanthan gum, triethanolamine, disodium edta, phenoxyethanol.

In a clinical study report, subjects tested the Luminate Eye Gel, applied to the periocul;ar area twice daily for a period of three months. A sample photograph showing improved appearance is provided in FIG. 1.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cosmetic composition for topical application comprising:
dimethylmethoxy chromanyl palmitate at a concentration of from 0.05-0.5%; palmitoyl tripeptide-1 at a concentration of from 0.0001-0.001%; palmitoyl tetrapeptide-7 at a concentration of from 0.0001-0.0005%; and a cosmetically acceptable vehicle.

2. The composition of claim 1, further comprising chrysin at a concentration of from 0.0001-0.001%.

3. The composition of claim 2, further comprising N-hydroxysuccinimide at a concentration of from 0.001-0.01%.

4. The composition of claim 3, further comprising linoleic acid at a concentration of from 0.1-1%; linolenic acid at a concentration of from 0.05-0.25%; tocopherol acetate at a concentration of from 0.1-1%; retinol at a concentration of from 0.01-0.075%; and ceramide-2 at a concentration of from 0.001-0.01%.

5. The composition of claim 4, wherein the cosmetically acceptable vehicle is a gel.

6. The composition of claim 5, wherein the gel is comprised of a mixture of cyclic siloxanes.

7. The composition of claim 6, wherein the cyclic siloxanes comprise from 75% to about 85% of the cosmetic composition.

8. The composition of claim 4, comprising by weight:
dimethylmethoxy chromanyl palmitate at a concentration of 0.1%; palmitoyl tripeptide-1 at a concentration of about 0.0002%; palmitoyl tetrapeptide-7 at a concentration of 0.0001%; chrysin at a concentration of 0.0002%; N-hydroxysuccinimide at a concentration of 0.004%; linoleic acid at a concentration of 0.4%; linolenic acid at a concentration of 0.1%; tocopherol acetate at a concentration of 0.5%; retinol at a concentration of 0.03%; and ceramide-2 at a concentration of 0.002%.

9. A method of improving the appearance of the skin of the periocular area, comprising:
topically applying a cosmetic composition comprising:
dimethylmethoxy chromanyl palmitate at a concentration of from 0.05-0.5%; palmitoyl tripeptide-1 at a concentration of from 0.0001-0.001%; palmitoyl tetrapeptide-7 at a concentration of from 0.0001-0.0005%; and a cosmetically acceptable vehicle.

10. The method of claim 9, wherein the composition further comprises chrysin at a concentration of from 0.0001-0.001%.

11. The method of claim 10, wherein the composition further comprises N-hydroxysuccinimide at a concentration of from 0.001-0.01%.

12. The method of claim 11, wherein the composition further comprises linoleic acid at a concentration of from 0.1-1%; linolenic acid at a concentration of from 0.05-0.25%; tocopherol acetate at a concentration of from 0.1-1%; retinol at a concentration of from 0.01-0.075%; and ceramide-2 at a concentration of from 0.001-0.01%.

13. The method of claim 9, wherein the cosmetically acceptable vehicle is a gel.

14. The method of claim 13, wherein the gel is comprised of a mixture of cyclic siloxanes.

15. The method of claim 14, wherein the cyclic siloxanes comprise from 75% to about 85% of the cosmetic composition.

16. The method of claim 9, wherein the composition further comprises by weight:
dimethylmethoxy chromanyl palmitate at a concentration of 0.1%; palmitoyl tripeptide-1 at a concentration of 0.0002%; palmitoyl tetrapeptide-7 at a concentration of 0.0001%; chrysin at a concentration of 0.0002%; N-hydroxysuccinimide at a concentration of 0.004%; linoleic acid at a concentration of 0.4%; linolenic acid at a concentration of 0.1%; tocopherol acetate at a concentration of 0.5%; retinol at a concentration of 0.03%; and ceramide-2 at a concentration of 0.002%.

* * * * *